(12) United States Patent
Zhu et al.

(10) Patent No.: US 10,751,176 B2
(45) Date of Patent: Aug. 25, 2020

(54) CONTROLLED BALLOON DEPLOYMENT

(71) Applicant: Edwards Lifesciences Corporation, Irvine, CA (US)

(72) Inventors: Yidong M. Zhu, Irvine, CA (US); PU Zhou, Irvine, CA (US); Erik Bulman, Lake Forest, CA (US); Baigui Bian, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 190 days.

(21) Appl. No.: 15/248,517

(22) Filed: Aug. 26, 2016

(65) Prior Publication Data

US 2017/0056170 A1 Mar. 2, 2017

Related U.S. Application Data

(60) Provisional application No. 62/210,375, filed on Aug. 26, 2015.

(51) Int. Cl.
*A61F 2/24* (2006.01)
*A61F 2/958* (2013.01)
*A61M 25/10* (2013.01)

(52) U.S. Cl.
CPC ............ *A61F 2/2433* (2013.01); *A61F 2/958* (2013.01); *A61M 25/104* (2013.01); *A61F 2250/0039* (2013.01); *A61M 25/10187* (2013.11); *A61M 2025/1059* (2013.01); *A61M 2025/1081* (2013.01)

(58) Field of Classification Search
CPC .. A61M 2025/1059; A61M 2025/1081; A61M 2025/1084; A61M 2025/1068; A61F 2/2433; A61F 2/958; A61F 2/962
See application file for complete search history.

(56) References Cited

U.S. PATENT DOCUMENTS

| 5,545,209 A * | 8/1996 | Roberts ................... A61F 2/958 |
| | | 604/103.05 |
| 2004/0073165 A1 | 4/2004 | Musbach et al. |
| 2007/0213663 A1 | 9/2007 | Wang |
| 2011/0190867 A1 | 8/2011 | Vonderwalde et al. |
| 2012/0083809 A1 | 4/2012 | Drasler et al. |

(Continued)

FOREIGN PATENT DOCUMENTS

| EP | 2450010 A1 | 5/2012 |
| WO | 2010022516 A1 | 3/2010 |

*Primary Examiner* — Diane D Yabut
*Assistant Examiner* — Majid Jamialahmadi
(74) *Attorney, Agent, or Firm* — Meunier Carlin Curfman LLC; Joel B. German

(57) ABSTRACT

The methods and devices disclosed herein promote temporal control of balloon inflation patterns. The devices include a covering for a portion of the balloon that compresses the balloon portion during the inflation process. This enables the distal portion of a balloon to be inflated prior to the proximal portion of a balloon, creating a tapered shape at lower inflation pressures. This is especially useful during transvascular implantation procedures, as it prevents dislodgement of an implant mounted on the balloon. As inflation continues, pressure exerted on the balloon by the covering is overcome such that the proximal region of the balloon inflates, forming a shape with generally straighter sides than the tapered shape, thereby expanding the cardiovascular device.

20 Claims, 5 Drawing Sheets

(56) References Cited

U.S. PATENT DOCUMENTS

| | | | |
|---|---|---|---|
| 2012/0116490 A1* | 5/2012 | Wesselmann | A61F 2/958 623/1.11 |
| 2013/0289607 A1 | 10/2013 | Pedersen et al. | |
| 2014/0142505 A1* | 5/2014 | Lin | A61M 25/1029 604/103.06 |

* cited by examiner

CONTROLLED BALLOON DEPLOYMENT

RELATED APPLICATIONS

This application claims the benefit of U.S. Provisional Application No. 62/210,375, filed Aug. 26, 2015, entitled "Expandable Balloon Sheath for Controlled Balloon Deployment," the disclosure of which is hereby incorporated by reference in its entirety.

FIELD

This invention relates generally to methods for controlled balloon inflation patterns during medical procedures that utilize inflatable balloons.

BACKGROUND

Balloons for delivering prosthetic cardiovascular devices or for performing dilation within the body are generally designed with a straight cylindrical, working length section and two symmetrical or nearly symmetrical cone regions at either end. The implant, such as a stent or implantable heart valve, is positioned over the working length section of the balloon for delivery. During inflation, the fluid first reaches the proximal portion of the balloon, an area that is not covered by the implantable heart valve, causing the proximal portion to inflate first. Inflation of the distal portion of the balloon is delayed until a path is opened by expansion of the implantable heart valve crimped onto the working length section of the balloon. This temporal inflation pattern can create risks, especially during a heart valve deployment procedure. For example, the implantable heart valve can be dislodged distally by the high pressure in the proximal portion of the balloon. The inflation pattern can also limit the ability of the physician to adjust the position of the implantable heart valve due to the risk of it dislodging from its preferred position on the balloon.

SUMMARY

The methods and devices disclosed herein promote temporal control of balloon inflation patterns. The devices include a covering for a portion of the balloon that compresses the balloon portion during the inflation process. This enables the distal portion of a balloon to be inflated prior to the proximal portion of a balloon, creating a tapered shape at lower inflation pressures. This is especially useful during transvascular implantation procedures, as it prevents dislodgement of an implant mounted on the balloon. As inflation continues, pressure exerted on the balloon by the covering is overcome such that the proximal region of the balloon inflates, forming a shape with generally straighter sides than the tapered shape, which expands the cardiovascular device.

The method of controlling expansion of a balloon includes flowing a fluid into the balloon and compressing a proximal region of the balloon by exerting pressure on the proximal region of the balloon with a covering, thereby inflating a distal region of the balloon before the proximal region of the balloon to form a tapering shape with an enlarged distal region. The method can further include continuing to flow fluid into the balloon and overcoming the pressure on the proximal region of the balloon. This can include progressively transitioning from flowing fluid into the distal region to flowing fluid into the proximal region, and the balloon can ultimately be inflated into a shape with generally straighter sides than the tapered shape.

In some implementations of the method of controlling expansion of a balloon, flowing the fluid into the balloon causes a rise in an inflation pressure. The step of inflating a distal region of the balloon before the proximal region of the balloon occurs at a first inflation pressure, and the step of inflating the balloon into a shape with generally straighter sides than the tapered shape occurs at a second inflation pressure. The second inflation pressure is higher than the first inflation pressure.

In some implementations of the method, the enlarged distal region of the balloon can have a distal diameter that is larger than a proximal diameter of the proximal region of the balloon when the inflation pressure is from 0.5 to 4 atmospheres. The ratio of the proximal diameter of the balloon to the distal diameter of the balloon can be 0.85 or greater at inflation pressures over 2.5 atmospheres.

In some implementations, the method of controlling expansion of a balloon can also include mounting an implantable cardiovascular device on the balloon before flowing the fluid into the balloon.

Methods of controlling the expansion of a balloon can take place within a patient vessel. These methods include inserting a balloon into the patient vessel, flowing a fluid into the balloon, and compressing a proximal region of the balloon by exerting pressure on the proximal region of the balloon with a covering and a cardiovascular device, thereby inflating a distal region of the balloon before the proximal region of the balloon to form a tapering shape with an enlarged distal region, anchoring the enlarged distal region of the tapering shape against a wall of the vessel, and continuing to flow fluid into the balloon to overcome the pressure on the proximal region of the balloon, thereby inflating the balloon to form a shape with generally straighter sides than the tapered shape and expanding the proximal region of the balloon toward the wall of the vessel.

The methods of controlling the expansion of a balloon within a patient vessel can further include repositioning the balloon after anchoring the enlarged distal region of the tapering shape of the balloon. In some implementations, the methods can further include anchoring the proximal region of the balloon against the wall of the vessel after overcoming the pressure on the proximal region of the balloon. The cardiovascular device can be a prosthetic heart valve or a stent.

Further disclosed herein is a controlled balloon deployment device. The controlled balloon deployment device includes a delivery catheter having a distal portion with a distal end, a balloon configured to move through the delivery catheter and to be deployed beyond the distal end of the delivery catheter, a cardiovascular device positioned around at least a portion of the balloon, and a covering extending through the distal portion of the delivery catheter and over at least a portion of the balloon. A portion of the covering is positioned between an outer surface of the balloon and an inner surface of the cardiovascular device when the balloon is deployed beyond the distal end of the delivery catheter. In some implementations, the covering extends through the distal portion of the delivery catheter and over a proximal portion of the balloon.

In some implementations of the controlled balloon deployment device, the covering is an expandable sheath. The sheath can include a polymer material. In some implementations, the cardiovascular device is a prosthetic heart valve or a stent.

In some implementations of the controlled balloon deployment device, the balloon has a tapered shape when in a partially inflated state. In the tapered, partially inflated state, the distal region of the balloon is larger than the proximal region of the balloon. In some implementations, the distal region of the balloon flares away from the cardiovascular device in the tapered, partially inflated state. In some implementations, the balloon has a shape with generally straighter sides than the tapered shape when in a fully inflated state.

DETAILED DESCRIPTION

Figure 1A:
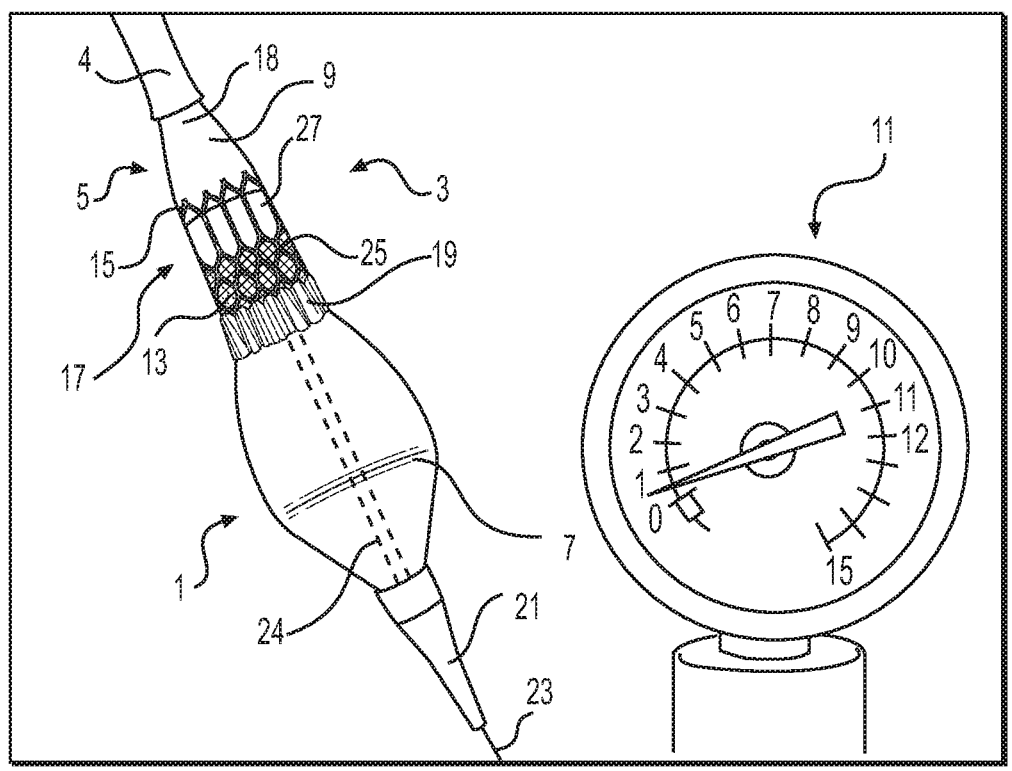
FIG. 1A shows a first frame in a series depicting the inflation of a balloon wherein the distal region of the balloon begins to inflate at the lowest pressure.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an" example of and is not intended to convey an indication of a preferred or ideal aspect. Such "as" is not used in a restrictive sense, but for explanatory purposes.

Disclosed herein are methods of controlling balloon expansion. Such methods are useful, for example, for delivering a device mounted on a balloon. Such devices can include, but are not limited to, cardiovascular devices or implants such as prosthetic implantable heart valves and stents. While delivery and implantation of a balloon-expandable implantable heart valve is described herein, it should be understood that the invention is not so limited. The methods include inflating a distal region of the balloon to form a tapering shape, positioning the balloon using the tapering shape, inflating a proximal region of the balloon to form a shape with generally straighter sides than the tapering shape to expand and anchor the implantable heart valve in position in the patient's body, then deflating and removing the balloon from the implantable heart valve. In some implementations, the proximal region of the balloon is compressed during inflation to achieve the tapering shape.

The terms "proximal" and "distal" as used herein refer to regions of the balloon, balloon catheter, or delivery catheter. "Proximal" means that region closest to handle of the device, while "distal" means that region farthest away from the handle of the device. The term "generally straighter sides" as used herein means a planar surface representative of the general path of the sides in the axial direction (averaging out any curves or non-linear aspects of the sides—such as by a least squares methodology) has less of an angle with respect to an axis extending through the balloon. Straight sides, for example, are when the sides have a zero degree angle, extending parallel to the axis of the balloon. Stated differently, the sides become generally straighter when the differential diameter between the proximal region and distal region decreases.

The term "vessel" as used herein refers to any structure surrounding a fluid passage, such as an artery, heart valve annulus or body lumen.

The methods disclosed herein promote temporal control of balloon inflation patterns, which is useful, for example, during transcatheter heart valve and stent implantation procedures. Particularly, the methods enable the distal portion of a balloon to be inflated prior to the proximal portion of a balloon, creating a tapered shape in both the balloon and the implantable device that prevents dislodging of the device from the balloon during the procedure. The methods can be performed in conjunction with implantable heart valve and stent delivery systems that are known in the art. However, use of the disclosed methods is not limited to currently known delivery systems.

FIGS. 1A-1D show a delivery balloon 1 with a stent mounted, implantable heart valve 3 mounted thereon. Balloon-expandable implantable heart valves are well-known and will not be described in detail here. An example of such an implantable heart valve is described in U.S. Pat. No. 5,411,552, and also in U.S. Patent Application Publication No. 2012/0123529, both of which are hereby incorporated by reference. The delivery balloon 1 and implantable heart valve 3 are delivered via delivery catheter 4. The delivery balloon is mounted on the distal end of the balloon catheter 24, which extends over guidewire lumen 23. The distal end of the balloon catheter is capped with a nosecone 21. The stent portion 25 of the implantable heart valve is positioned around the valve portion 27 of the implantable heart valve 3.

It should be noted that the positioning of the heart valve on the balloon can vary depending on the route of delivery. As will be explained in greater detail below, in typical transcatheter heart valve implantation where the valve is delivered transfemorally, the valve is positioned with its inflow end at the distal end of the balloon. When the valve is delivered transapically, the position of the valve on the balloon is reversed, i.e., the inflow end of the valve is positioned on the proximal end of the balloon. Thus, while FIGS. 1A-1D depict a transcatheter aortic valve having on outer skirt positioned on the inflow end of the valve, which is in turn positioned on the distal end of the balloon, the position of the valve of the balloon can vary. Thus, the figures are illustrative of only one implantation and are not intended to be limiting.

Certain embodiments of balloon expandable implantable heart valves, such as the one shown in FIGS. 1A-D, include an outer skirt 19 for minimizing paravalvular leakage. An example of such a valve is described in U.S. Pat. No. 9,393,110 which is incorporated by reference herein. As noted above, however, the methods disclosed herein could be used to deliver other types of implants, such as, for example, annuloplasty devices or stents, and are also useful in other applications where variable balloon diameters are desired such as angioplasty or valvuloplasty procedures or any other procedure where a dilation balloon is used. The balloon 1 has a distal region 7 and a proximal region 9. Generally, the distal region 7 is any part (but not necessarily all) of the balloon 1 distal of its midline or the middle of its length in the axial direction. The proximal region 9 is any part of the balloon 1 proximal its midline or the middle of its length in the axial direction. The term "end" on the other hand refers to a portion of a structure closer to its end than just starting on one side of the mid-line. But, the term "end" need not be the furthest portion or free end of a structure. An "end" can be any portion at or near the end.

In the implementation of FIGS. 1A-1D, the proximal region 9 of the balloon 1 is covered by a covering. In this example, the covering is an expandable sheath 5. The sheath 5 is preferably made from a very thin polymer. For example, the sheath 5 may be formed of latex, polyether, urethane, or Neusoft™. The sheath 5 material has increased opacity compared to the balloon material. This increased opacity prevents clear visualization of the balloon catheter 24 through the proximal region 9 of the balloon.

The covering or sheath 5 can include a taper at its distal portion 17. The taper flares outward from a longitudinal axis running through the lumen of the sheath 5. For example, the sheath 5 has a taper and extends underneath the implantable heart valve 3, as shown in FIG. 1A. Generally, sheaths with longer tapers have a greater tendency to stay on the balloon 1 as it is inflated—a long distal portion 17 of the sheath 5 covers the balloon 1 and is trapped under the implantable heart valve 3. Sheaths with shorter tapers, on the other hand, may be designed to roll off the proximal end 9 of the balloon 1 as it inflates. The sheath 5 that has rolled off can be easily withdrawn from the balloon 1. A sheath 5 that has not rolled off is elastic and can collapse with the balloon 1 for withdrawal with the balloon catheter.

Figure 1B:
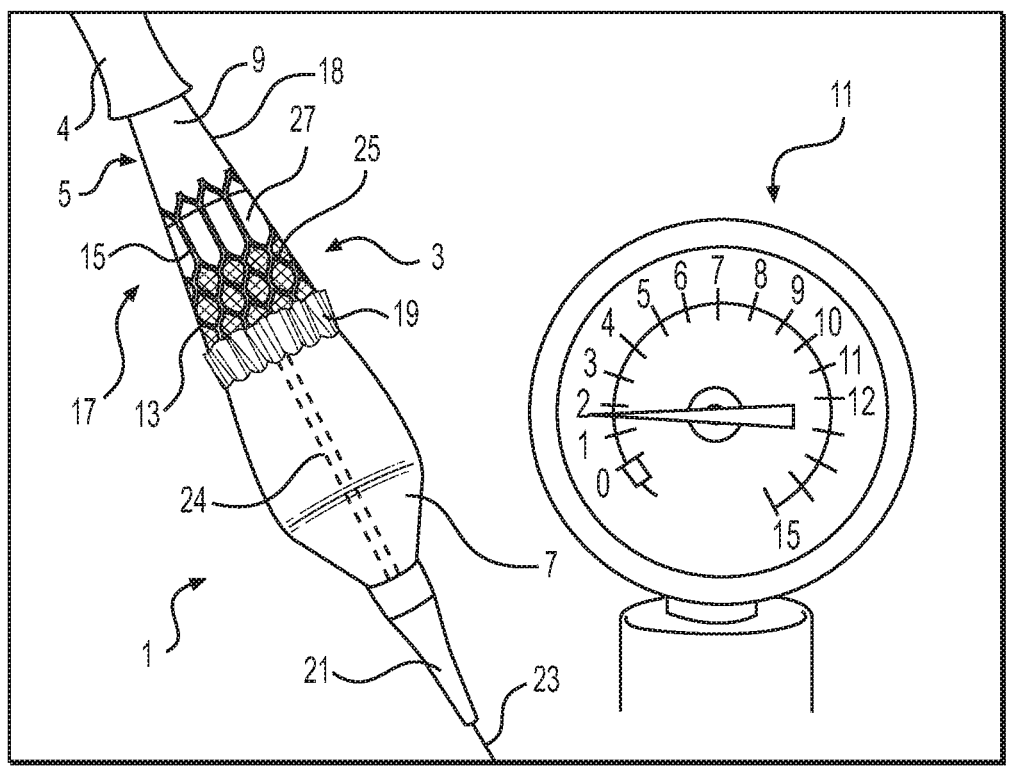
FIG. 1B shows a second frame in the series depicting the inflation of a balloon of FIG. 1A wherein the heightened pressure causes the proximal region of the balloon to commence inflation.

The distal portion 17 of the covering or expandable sheath 5 is preferably positioned between the outer surface of the balloon 1 and the inner surface of the implantable heart valve 3. This helps to mediate the dilation and pressure of the proximal region 9 of the balloon 1, reducing somewhat the load on the inner surface of the implantable heart valve 3. As shown in FIG. 1B, the implantable heart valve 3 does not extend onto the distal region 7 of the balloon 1. Instead, it extends around the sheath 5 on the proximal region 9 of the balloon 1. The proximal portion 18 of the sheath 5 extends from the proximal end of the balloon 1, past the distal end of the delivery catheter 4, and into the distal portion of a delivery catheter 4. In this manner, the sheath 5 can be maneuvered by manipulation of the proximal end of the delivery catheter 4.

Generally, the material and thickness of the wall of the sheath 5 can be varied so as to provide enough hoop stress to restrain the proximal region 9 of the balloon 1 during the inflation pressure of the beginning of the inflation cycle. Thinner materials, for example, need to be somewhat stiffer while thicker materials can have a lower stiffness. Thinner walls for the sheath 5 have some advantage of minimizing the diameter of the entire delivery system and of fitting more easily between the implantable heart valve 3 and the balloon 1.

A pressure gauge, 11, is also shown in FIG. 1A. In the series of figures that follow (FIGS. 1B-1D), the pressure indicated by pressure gauge 11 increases (representationally as opposed to having exact numbers) as the balloon 1 is inflated with a fluid.

To facilitate the methods disclosed herein, a physician (or other healthcare worker) first accesses the procedure site using a transvascular approach. For example, the procedure site can be accessed transfemorally, transaortically, or transapically. Prior to or during delivery, the implantable heart valve 3 or other implant is crimped or compressed onto the deflated balloon 1, or moved onto the balloon 1 once in the patient's body, to keep the overall profile of the delivery system to a minimum. When the implantation site is reached, the physician begins to inflate balloon 1 bearing the prosthetic heart valve 3. As shown in FIG. 1A, the compression of the proximal region 9 of the balloon 1 by the sheath 5, and the heart valve 3, causes the distal region 7 of the balloon 1 to inflate before the proximal region 9. This creates a tapering shape of both the balloon 1 and the implantable heart valve 3, where the walls are generally more angled, rather than straight or parallel to the long axis of the balloon 1.

Figure 1C:
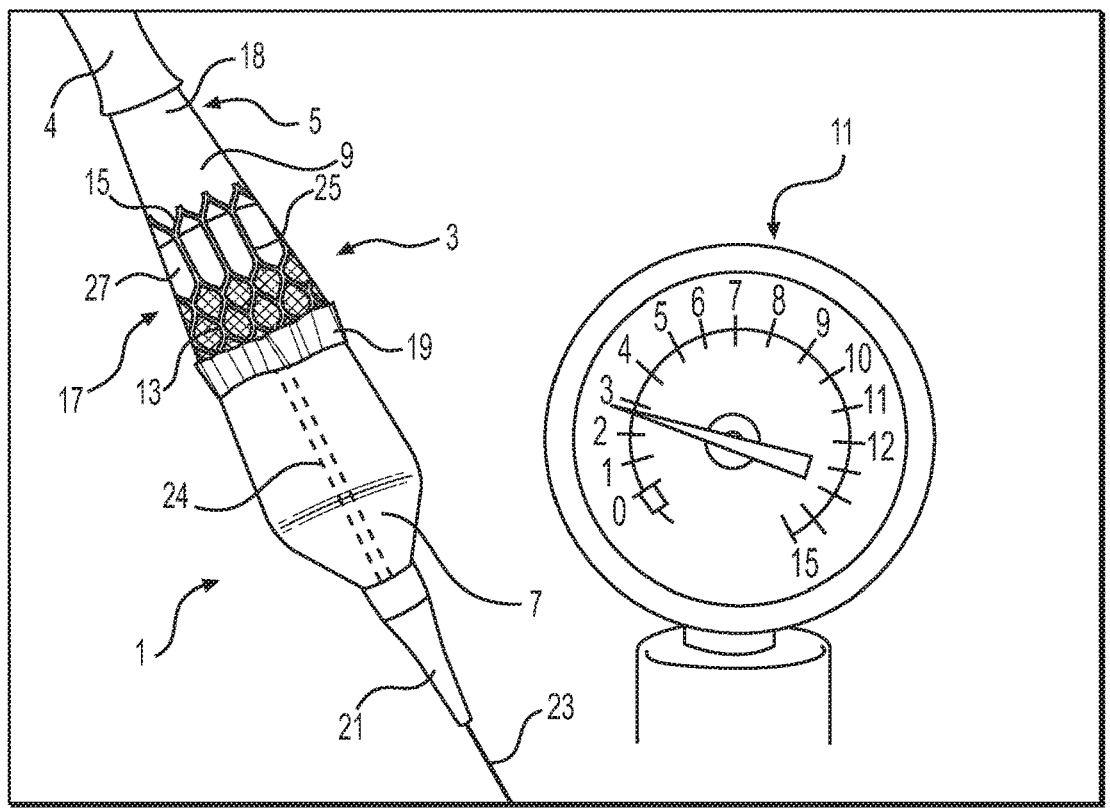
FIG. 1C shows a third frame in the series depicting the inflation of a balloon of FIGS. 1A-B wherein the difference in diameter between the proximal and distal regions of the balloon is smaller than in the first or second frames.
Figure 1D:
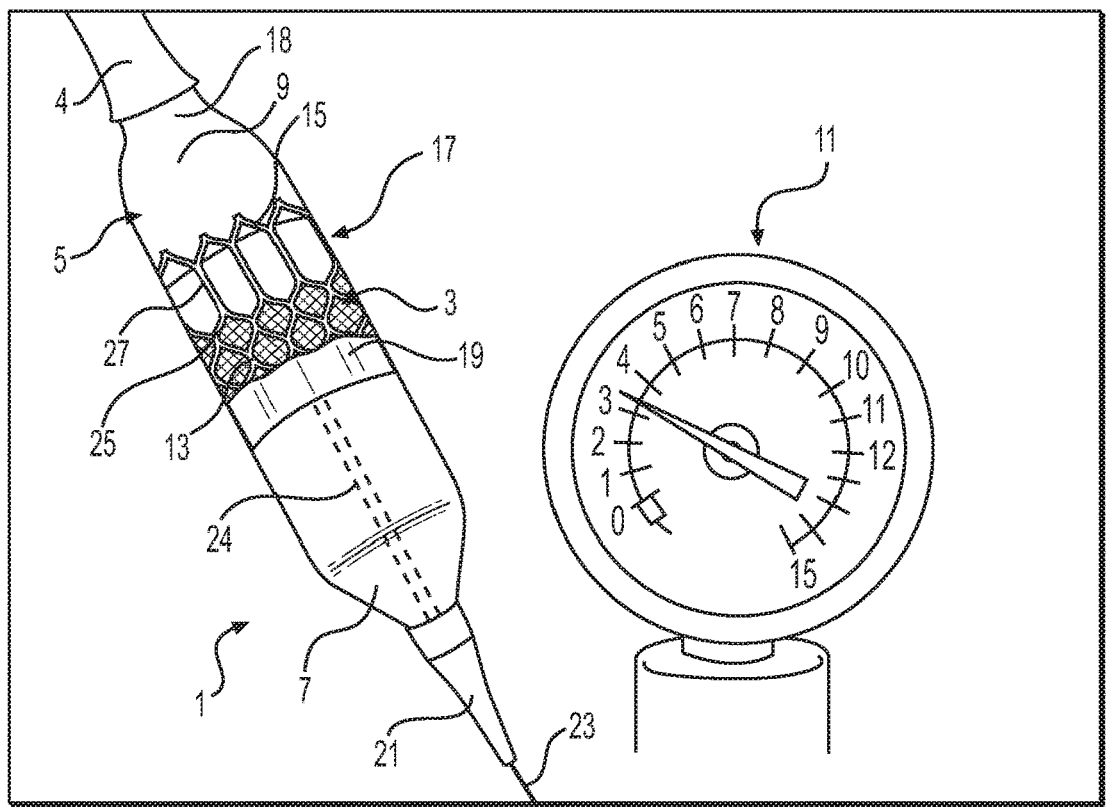
FIG. 1D shows a fourth frame in the series depicting the inflation of a balloon of FIGS. 1A-C wherein the difference in diameter between the proximal and distal regions of the balloon is smaller than in the previous frames.

A progressive transition from inflating the distal region 7 to inflating the proximal region 9 then occurs, as shown in FIGS. 1B-1D. As shown in FIG. 1B, the proximal region 9 of the balloon 1 begins to expand as the inflation pressure increases and overcomes the pressure that the implantable heart valve 3 and the expandable sheath 5 exert on the surface of the balloon 1. The angle of the tapering shape (between the angle between the balloon walls and a longitudinal axis running from the proximal to distal ends of the balloon 1) decreases as the inflation pressure rises until the balloon 1, and thus the implantable heart valve 3, is less tapered or not tapered at all. In some implementations, the method enables a distal end 13 of the implantable heart valve 3 to be anchored prior to anchoring a proximal end 15 of the implantable heart valve 3. A total elimination of taper is not necessary for advantages such as controlled anchoring of the balloon 1, reduction of migration of the implantable heart valve 3 and/or movement of the implantable heart valve 3 to a new position. For example, halting distal and proximal migration of the implantable heart valve 3 with respect to the balloon 1 can be impeded by some slight straightening of the sides. Even slight straightening will improve the friction between the balloon 1 and implantable heart valve 3. Slight straightening might also, for example, bring some surface features into operable engagement with the implantable heart valve 3 for improved anchoring. On the other hand, less taper generally helps with control, anchoring and placement of implantable heart valves.

Figure 2:
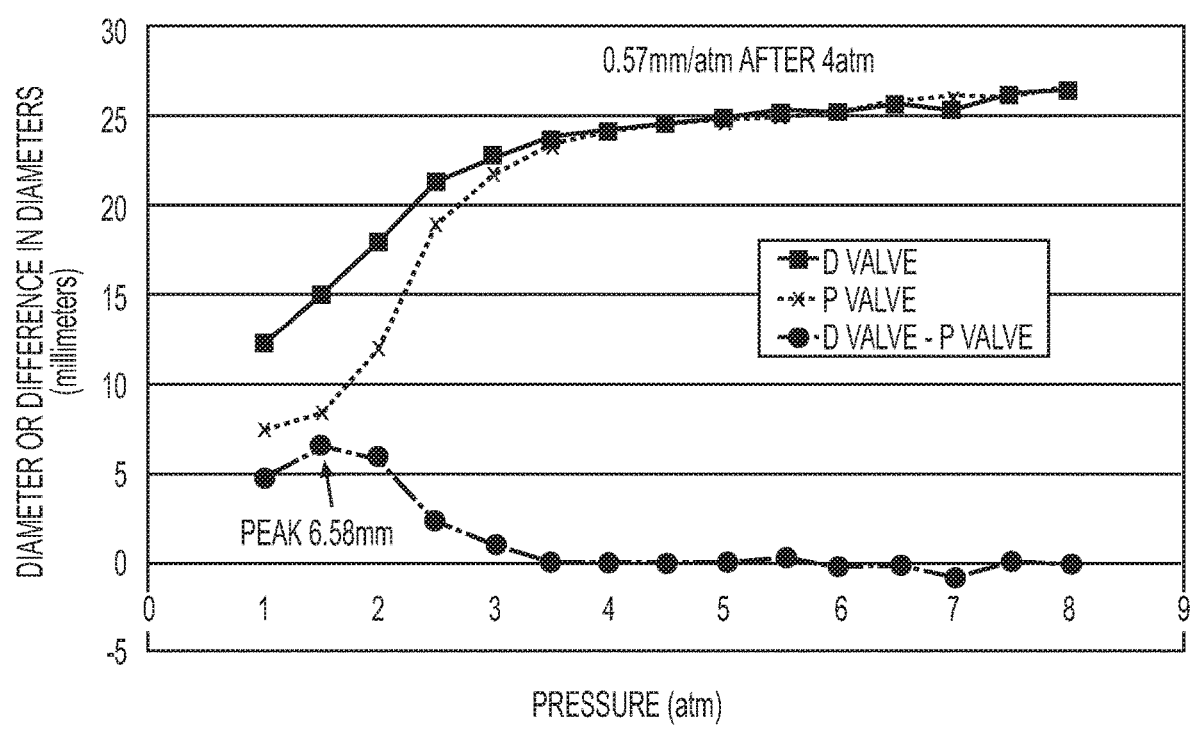
FIG. 2 shows a line graph of the proximal and distal diameters of a stent mounted implantable heart valve mounted on the balloon at different inflation pressures, and also the difference between the proximal and distal diameters of the valve at different inflation pressures.
Figure 3A:
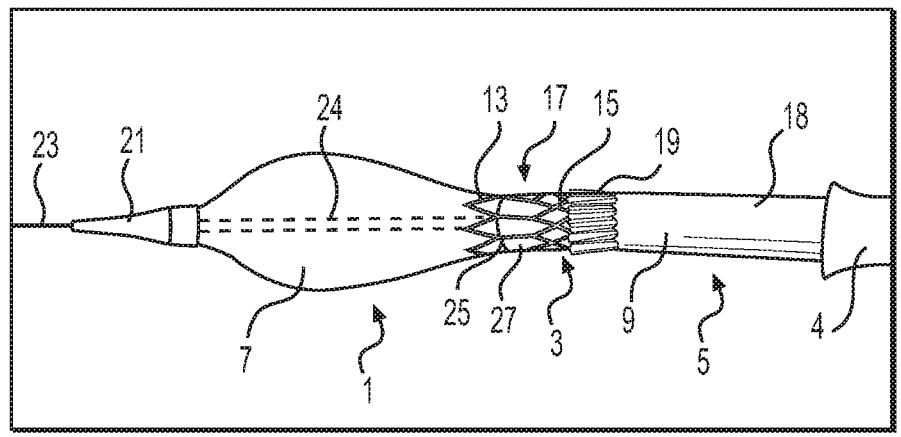
FIG. 3A shows a first frame in a series depicting the inflation of a balloon having a stent mounted implantable heart valve positioned thereon such that the implantable heart valve's distal end extends over the distal edge of the sheath and begins to inflate at the lowest pressure.
Figure 3B:
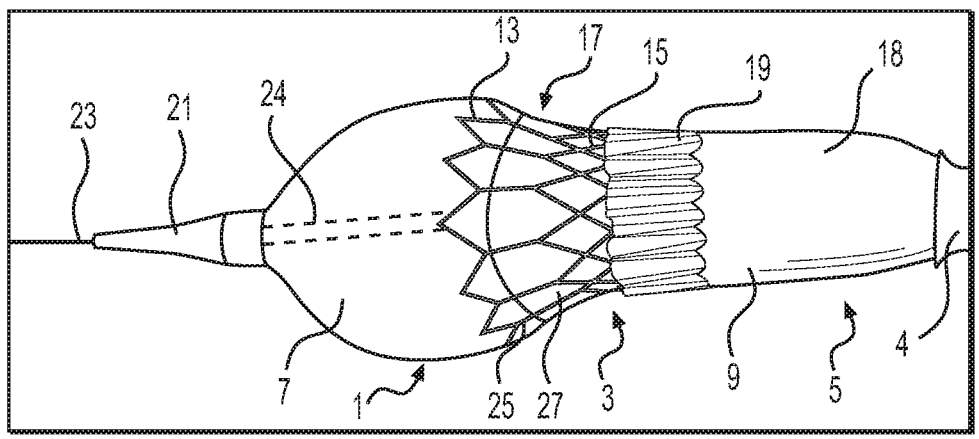
FIG. 3B shows a second frame in the series depicting the inflation of a balloon of FIG. 3A wherein the heightened pressure causes the proximal region of the balloon to commence inflation.
Figure 3C:
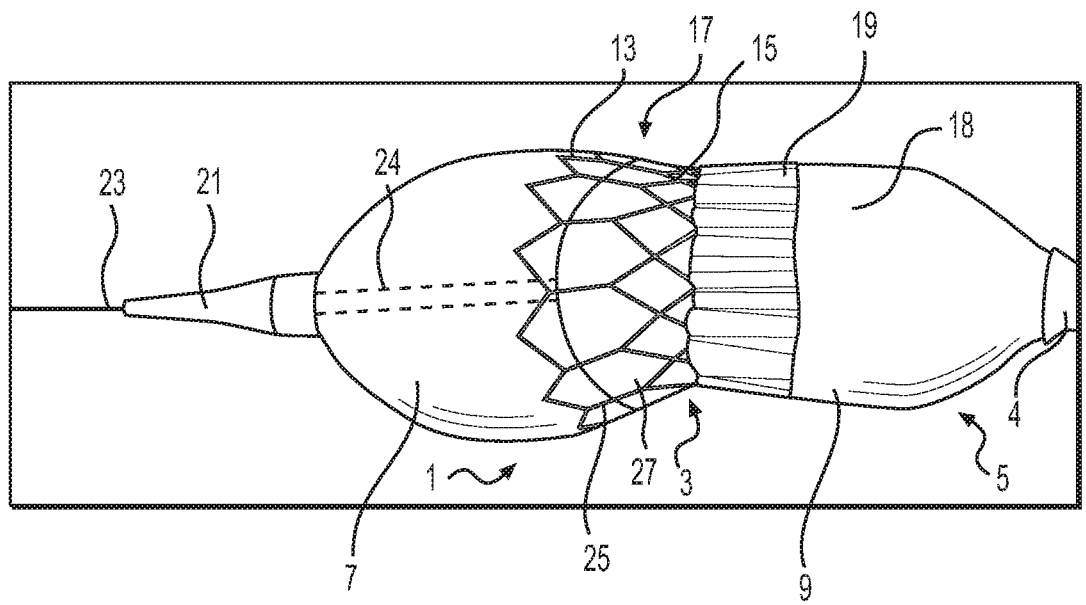
FIG. 3C shows a third frame in the series depicting the inflation of a balloon of FIGS. 3A-B wherein the difference in diameter between the proximal and distal regions of the balloon is smaller than in the first or second frames.
Figure 3D:
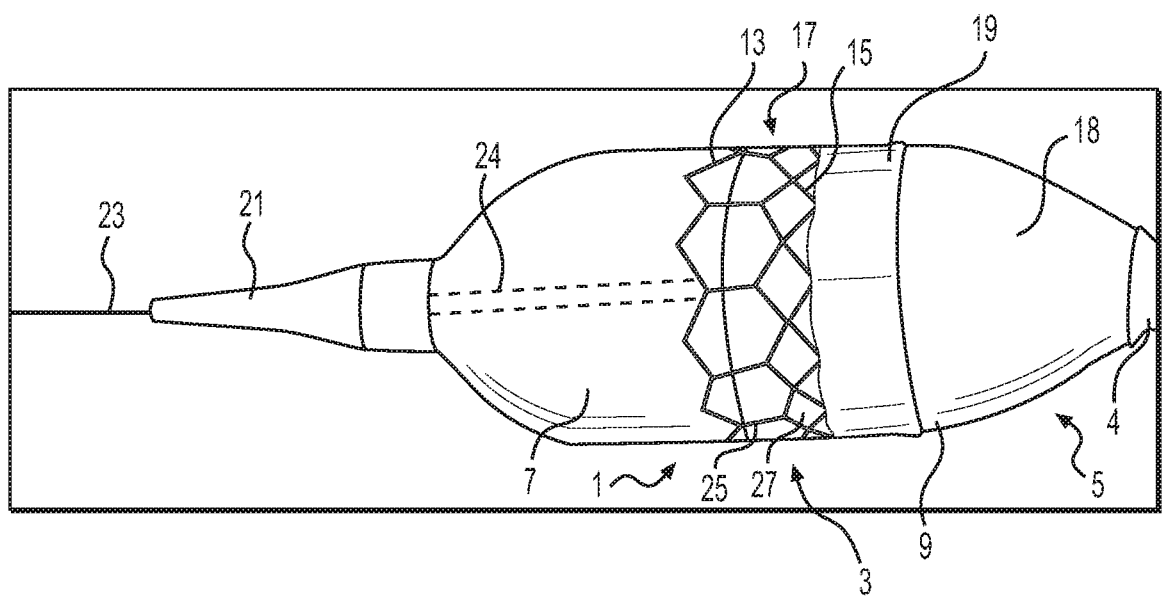
FIG. 3D shows a fourth frame in the series depicting the inflation of a balloon of FIGS. 3A-C wherein the difference in diameter between the proximal and distal regions of the balloon is smaller than the previous frames.

In some implementations, a diameter of the distal region 7 of the balloon 1 will be larger than a diameter of the proximal region 9 of the balloon 1 when the inflation pressure ranges from 0.5 to 4 atmospheres. In some implementations, a ratio of a proximal diameter of the balloon 1 to a distal diameter of the balloon 1 is 0.85 or greater at inflation pressures over 2.5 atmospheres. Table 1 shows the proximal and distal diameters of the balloon 1 and mounted implantable heart valve 3 at different inflation pressures. As shown in the far right hand column, the difference between the distal and proximal diameters of the implantable heart valve 3 decreases as the inflation pressure increases. FIG. 2 illustrates this data as a line graph.

TABLE 1

| pressure (ATM) | distal (D) balloon diameter (mm) | proximal (P) balloon diameter (mm) | distal (D) valve diameter (mm) | proximal (P) valve diameter (mm) | D valve − P valve |
|---|---|---|---|---|---|
| 1.00 | 21.58 | 8.78  | 12.34 | 7.59  | 4.75  |
| 1.50 | 21.68 | 13.34 | 15.00 | 8.42  | 6.58  |
| 2.00 | 22.02 | 15.35 | 18.03 | 12.10 | 5.93  |
| 2.50 | 22.57 | 19.65 | 21.30 | 18.99 | 2.31  |
| 3.00 | 22.72 | 21.65 | 22.74 | 21.70 | 1.04  |
| 3.50 | 23.30 | 23.36 | 23.61 | 23.43 | 0.18  |
| 4.00 | 23.44 | 22.93 | 24.10 | 24.09 | 0.01  |
| 4.50 | 24.20 | 23.46 | 24.57 | 24.42 | 0.15  |
| 5.00 | 24.53 | 23.85 | 24.82 | 24.67 | 0.15  |
| 5.50 | 24.71 | 24.31 | 25.15 | 24.80 | 0.35  |
| 6.00 | 25.01 | 24.61 | 25.15 | 25.25 | −0.10 |
| 6.50 | 25.38 | 24.92 | 25.57 | 25.66 | −0.09 |
| 7.00 | 25.43 | 25.21 | 25.33 | 25.98 | −0.65 |
| 7.50 | 25.57 | 25.25 | 26.11 | 25.99 | 0.12  |
| 8.00 | 25.90 | 25.70 | 26.33 | 26.38 | −0.05 |

The methods disclosed herein prevent migration of the implantable heart valve 3 during the procedure by flaring the distal region 7 of the balloon 1 away from the implantable heart valve 3. The tapered shape of the balloon 1 acts as a locking mechanism that keeps the implantable heart valve 3 from dislodging during the implantation procedure. For example, in a transcatheter aortic heart valve implantation, where the implantable heart valve 3 is delivered transfemorally and across the aortic annulus, the distal end of the balloon 1 having the implantable heart valve 3 mounted thereon is positioned inside the left ventricular outflow tract (LVOT).

The embodiment shown in FIGS. 1A-1D is designed to be delivered transfemorally, and thus the implantable heart valve outer skirt 19 is on the distal end 13 of the implantable heart valve 3 so that it may be positioned on the ventricular side of the aortic annulus. When the distal end of the balloon 1 is inflated first, it allows the distal or inflow end of the implantable heart valve 3 to anchor first. As the balloon 1 continues to inflate and expand, the implantable heart valve 3 undergoes controlled deployment until assuming its final, less tapered shape (a shape with generally straighter sides than the tapered shape) that provides the best hemodynamics for the patient. In some procedures, the physician must reposition the implantable heart valve 3 after inflating the balloon 1. The back and forth motion within the annulus or lumen raises the risk that the implantable heart valve 3 will be dislodged from its preferred position on balloon 1. The tapered shape prevents this from happening.

FIGS. 3A-D show another implementation of a delivery system including an implantable heart valve 3 mounted on balloon 1 designed for transapical delivery. The proximal end 9 of balloon 1 is covered by the distal end 17 of sheath 5, as in FIGS. 1A-D. However, because the native valve is approached from the opposite direction (through the left ventricle and LVOT) in a transapical procedure, the implantable heart valve 3 is mounted onto the balloon 1 such that the outer skirt 19 is on the proximal end 15 of the implantable heart valve 3. Like the transfemoral method described above, the distal region 7 of the balloon 1 is inflated first. However, the distal end 7 of the balloon 1 is positioned within the aorta during inflation for the transapical approach, instead of within the left ventricle.

In some implementations of the methods, such as the one shown in FIGS. 3A-3D, the implantable heart valve 3 is positioned such that its distal end 13 extends beyond the distal end 17 of the sheath 5. Because of its heightened proximity to the distal region 7 of the balloon 1, the distal end 13 of the implantable heart valve 3 expands at a lower inflation pressure than when the entire implantable heart valve 3 is positioned over the covering or sheath 5. This causes the distal end 13 of the implantable heart valve 3 to flare outward earlier during the process of inflating the balloon 1, anchoring the distal end 13 of the implantable heart valve 3 first. Progressive inflation of the balloon then anchors the proximal end 15 of the implantable heart valve 3.

Once the implantable heart valve 3 is securely anchored inside the patient's body, the balloon 1 is deflated and removed from the patient. The balloon 1 may be deflated, for example, by draining or removing the fluid from the balloon 1 to collapse the balloon 1 into a smaller diameter.

While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular implementations disclosed herein, but that the invention will include all implementations falling within the scope of the appended claims.

What is claimed is:

1. A method of controlling expansion of a balloon, the method comprising:
   flowing a fluid into the balloon,
   compressing a proximal region of the balloon by exerting pressure on the proximal region of the balloon with an elastic covering over the proximal region of the balloon, wherein the proximal region is proximal to a midline of the balloon in an axial direction, thereby inflating a distal region of the balloon before the proximal region of the balloon to form a tapering shape with an enlarged distal region;
   wherein the elastic covering of the balloon does not extend distal of the midline of the balloon.

2. The method of claim 1, further comprising continuing to flow fluid into the balloon and overcoming the pressure on the proximal region of the balloon.

3. The method of claim 2, further comprising inflating the balloon into a shape with generally straighter sides than the tapered shape.

4. The method of claim 2, wherein continuing to flow fluid comprises progressively transitioning from flowing fluid into the distal region to flowing fluid into the proximal region.

5. The method of claim 2, wherein flowing the fluid into the balloon causes a rise in an inflation pressure, wherein inflating the distal region of the balloon before the proximal region of the balloon occurs at a first inflation pressure, and wherein inflating the balloon into a shape with generally straighter sides than the tapered shape occurs at a second inflation pressure that is higher than the first inflation pressure.

6. The method of claim 5, wherein the enlarged distal region of the balloon has a distal diameter that is larger than a proximal diameter of the proximal region of the balloon when the inflation pressure is from 0.5 to 4 atmospheres.

7. The method of claim 6, wherein a ratio of the proximal diameter of the balloon to the distal diameter of the balloon is 0.85 or greater at inflation pressures over 2.5 atmospheres.

8. The method of claim 1, further comprising mounting a cardiovascular device on the balloon before flowing the fluid into the balloon.

9. The method of claim 1, wherein the elastic covering includes a taper at its distal end, the taper flaring outwards from a longitudinal axis of the elastic covering.

10. The method of claim 9, wherein the taper extends under the cardiovascular device.

11. The method of claim 1, wherein the elastic covering is removed from at least a portion of the proximal region of the balloon as fluid flows into the balloon and inflates.

12. The method of claim 1, wherein the elastic covering rolls off of at least a portion of the proximal region of the balloon as fluid flows into the balloon and inflates.

13. A method of controlling expansion of a balloon within a patient vessel, the method comprising:
    inserting a balloon into the patient vessel, the balloon having a cardiovascular device mounted thereon;
    flowing a fluid into the balloon;
    compressing a proximal region of the balloon by exerting pressure on the proximal region of the balloon with an elastic covering over the proximal region of the balloon, wherein the proximal region is proximal to a midline of the balloon in an axial direction, thereby inflating a distal region of the balloon before the proximal region of the balloon to form a tapering shape with an enlarged distal region, wherein the elastic covering of the balloon does not extend distal of the midline of the balloon;
    anchoring the enlarged distal region of the tapering shape against a wall of the vessel;
    continuing to flow fluid into the balloon;
    overcoming the pressure exerted by the elastic covering on the proximal region of the balloon, thereby inflating the balloon to form a shape with generally straighter sides than the tapered shape, expanding the proximal region of the balloon toward the wall of the vessel, and expanding the cardiovascular device.

14. The method of claim 13, further comprising repositioning the balloon after anchoring the enlarged distal region of the tapering shape of the balloon.

15. The method of claim 13, further comprising anchoring the proximal region of the balloon against the wall of the vessel after overcoming the pressure on the proximal region of the balloon.

16. The method of claim 13, wherein the cardiovascular device is a prosthetic heart valve or a stent.

17. The method of claim 13, wherein the elastic covering includes a taper at its distal end, the taper flaring outwards from a longitudinal axis of the elastic covering.

18. The method of claim 17, wherein the taper extends under the cardiovascular device.

19. The method of claim 13, further comprising removing the elastic covering from at least a portion of the proximal region of the balloon as the pressure exerted by the elastic covering is overcome.

20. The method of claim 13, further comprising rolling the elastic covering off of at least a portion of the proximal region of the balloon as the pressure exerted by the elastic covering is overcome.

* * * * *